(12) United States Patent
Welch

(10) Patent No.: US 7,795,591 B2
(45) Date of Patent: Sep. 14, 2010

(54) DUAL-CAPILLARY OBTURATOR FOR REAL-TIME VERIFICATION IN GAMMA GUIDED STEREOTACTIC LOCALIZATION

(75) Inventor: Benjamin L. Welch, Hampton, VA (US)

(73) Assignee: Dilon Technologies, Inc., Newport News, VA (US)

( * ) Notice: Subject to any disclaimer, the term of this patent is extended or adjusted under 35 U.S.C. 154(b) by 184 days.

(21) Appl. No.: 12/218,575

(22) Filed: Jul. 16, 2008

(65) Prior Publication Data

US 2010/0012847 A1 Jan. 21, 2010

(51) Int. Cl.
*G01T 1/166* (2006.01)
(52) U.S. Cl. .................. 250/363.04; 382/131; 600/566; 606/170
(58) Field of Classification Search ............ 250/363.04, 250/670.09, 363.1
See application file for complete search history.

(56) References Cited

U.S. PATENT DOCUMENTS

| | | | | |
|---|---|---|---|---|
| 4,006,735 A | * | 2/1977 | Hittman et al. | 600/561 |
| 5,803,913 A | * | 9/1998 | Khalkhali et al. | 600/407 |
| 5,864,141 A | * | 1/1999 | Majewski et al. | 250/363.02 |
| 6,173,201 B1 | * | 1/2001 | Front | 600/429 |
| 6,424,693 B1 | * | 7/2002 | Weisenberger | 378/37 |
| 2006/0074345 A1 | * | 4/2006 | Hibner | 600/566 |

\* cited by examiner

*Primary Examiner*—David P Porta
*Assistant Examiner*—Djura Malevic

(57) ABSTRACT

A combination rigid grid positioning system, stereotactic gamma imager and an obturator for real-time localization of a region of interest during the performance of a surgical procedure including: a) a rigid grid positioning system including a mechanism for the acquisition of images useful in calculating the spatial location of a region of interest in a mass under study; and b) an obturator inserted through the rigid grid positioning system made up of: i) first and second generally parallel capillary tubes for the introduction thereto and the removal therefrom of a radioactive fluid interconnected at a point of connection; and ii) a reservoir for the radioactive fluid at the point of connection; wherein the reservoir is inserted into the mass containing a region of interest and the radioactive fluid provides a marker for the region of interest during subsequent imaging and thereby specific localization of the region of interest during subsequent procedures.

6 Claims, 3 Drawing Sheets

DUAL-CAPILLARY OBTURATOR FOR REAL-TIME VERIFICATION IN GAMMA GUIDED STEREOTACTIC LOCALIZATION

FIELD OF THE INVENTION

The present invention relates to gamma guided stereotactic imaging and more particularly to an obturator device for verifying image location and to a method of use thereof.

BACKGROUND OF THE INVENTION

Gamma guided stereotactic imaging/localization uses two gamma camera images of an object taken at different angles to determine the three dimensional location of the region of interest in that object. The location can be used, for example, for positioning a needle in a suspected tumor to collect a tissue sample for biopsy. In some situations, it is desirable to have real-time verification of the location during the procedure. This requires that a marker be placed at the location of the region of interest. In order to be imaged by the gamma camera, the marker must be radioactive, and capable of removal without leaving contamination and should be seen in the image at the time of verification.

Thus, there is a need for a system or method and device for providing such a marker for purposes of real-time localization during gamma imaging.

OBJECT OF THE INVENTION

It is therefore an object of the present invention to provide both a device and a method for the provision of real-time localization information during stereotactic gamma imaging.

SUMMARY OF THE INVENTION

The present invention provides a combination rigid grid positioning system, stereotactic gamma imager, and an obturator for real-time localization of a region of interest during the performance of a surgical procedure including: a) a rigid grid positioning system including a mechanism for the acquisition of images useful in calculating the spatial location of a region of interest in a mass under study; and b) an obturator inserted through the rigid grid positioning system made up of: i) first and second generally parallel capillary tubes for the introduction thereto and the removal therefrom of a radioactive fluid interconnected at a point of connection; and ii) a reservoir for the radioactive fluid at the point of connection; wherein the reservoir is inserted into the mass containing a region of interest and the radioactive fluid provides a marker for the region of interest during subsequent imaging and thereby specific localization of the region of interest during subsequent procedures.

DETAILED DESCRIPTION

Figure 1:
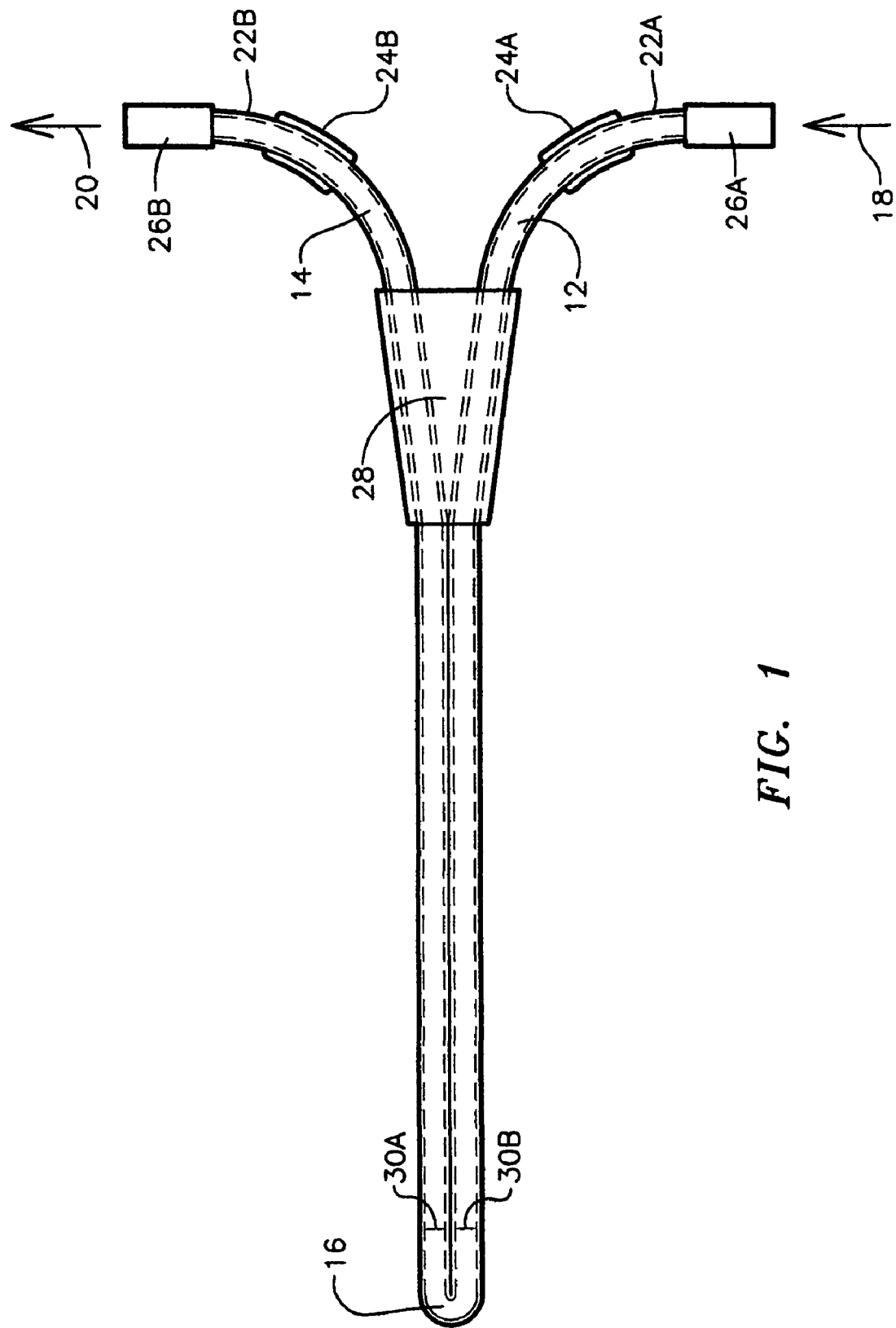
FIG. 1 is a partially phantom view of an obturator in accordance with the present invention.

Referring now to the accompanying drawings, as shown in FIG. 1, the obturator 10 of the present invention comprises a pair of generally parallel and interconnected capillary tubes 12 and 14 joined at a reservoir 16 at their point of connection. Capillary tube 12 permits filling of obturator 10 as indicated by arrow 18, while capillary tube 14 acts as a vent for the removal of fluid introduced into tube 12 in the direction indicated by arrow 20. The point of junction of capillaries 12 and 14 comprises reservoir 16. One or more mechanisms 24A and 24B can be provided to seal the ends 22A and 22B of capillary tubes 12 and 14. Similarly, connectors/fittings 26A and 26B can be provided to permit attachment of syringes or other devices for the introduction and removal of a measured quantity of radioactive fluid. Capillary tubes 12 and 14 are preferably fabricated from a flexible transparent material that permits viewing of the incorporated radioactive fluid and allows for at least minimal manipulation of capillary tubes 12 and 14. Capillary tubes 12 and 14 are fabricated with a material that exhibits higher attenuation of the radioactive emissions produced by the radioactive fluid than that which forms reservoir 16. For example, capillary tubes 12 and 14 can be fabricated from a tungsten powder impregnated glass or polymer while reservoir 16 is fabricated from unimpregnated glass or polymer. Finally, required, a mechanism 28 may be provided to maintain the unity of capillary tubes 12 and 14 in obturator 10. According to a preferred embodiment of the present invention, only sufficient radioactive fluid is introduced into capillary tubes 12 and 14 to fill reservoir 16, as, for example, by filing to the levels indicated by dotted lines 30A and 30B. Capillary tubes 12 and 14 are of a size such that their combined diameter is that of a standard needle as used in surgical procedures. The radioactive fluid utilized will, of course, be dependent upon the particular test or imaging procedure being conducted.

Figure 2:
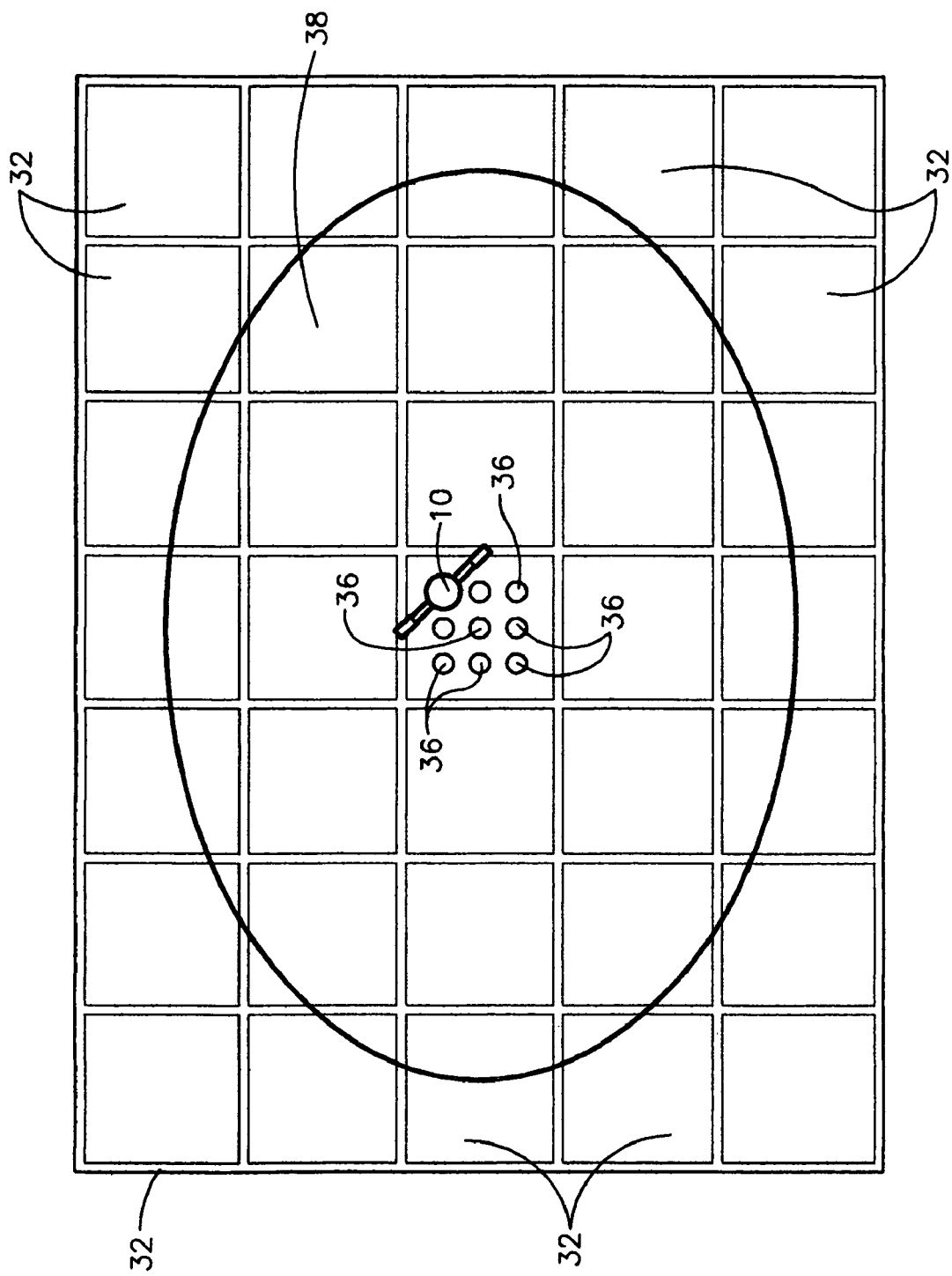
FIG. 2 is a top plan view of the obturator of the present invention inserted through a grid positioning system in accordance with the present invention.
Figure 3:
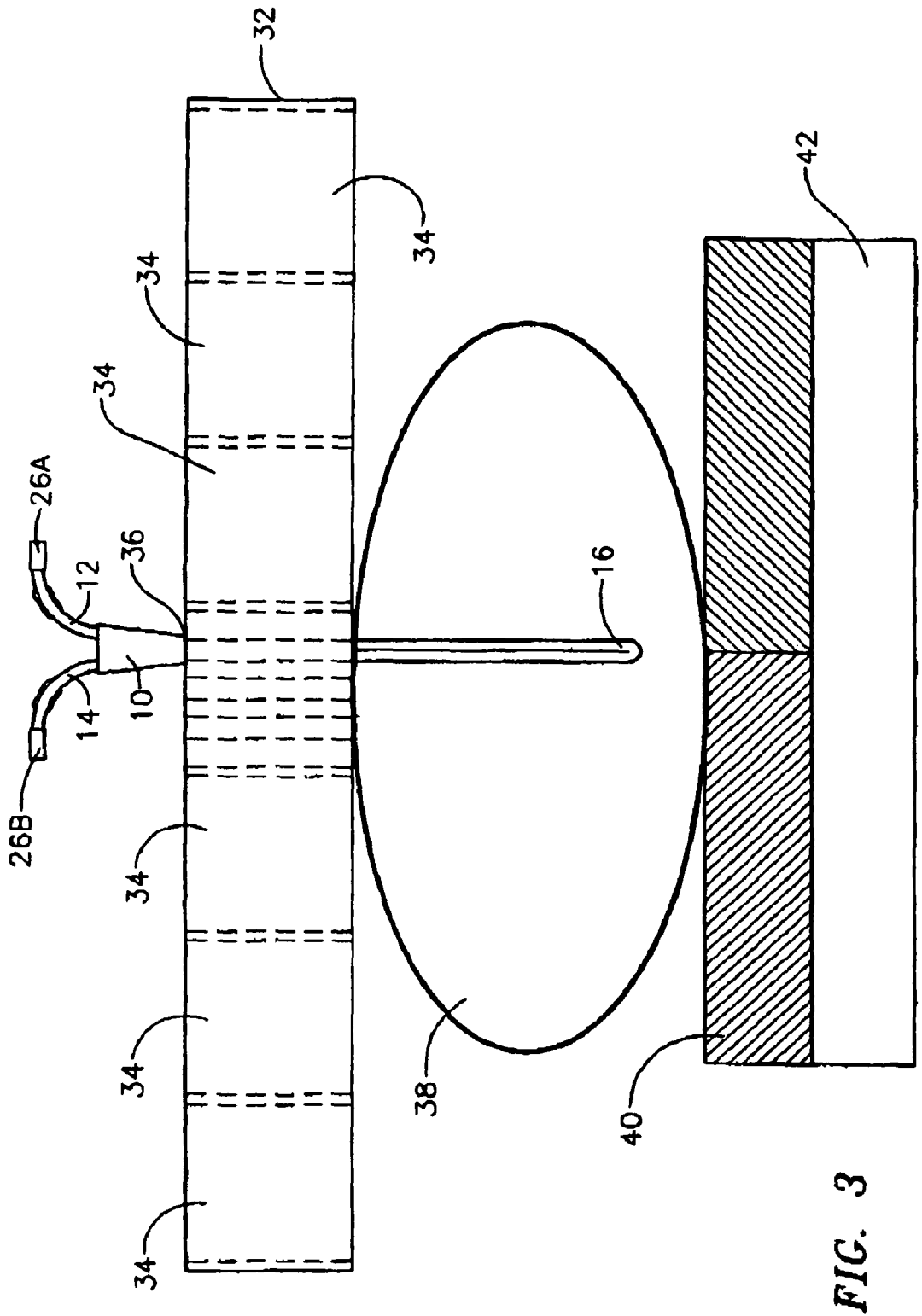
FIG. 3 is a cross-sectional view of the obturator of the present invention in use in localizing a region of interest in a mass under study.

As shown in FIGS. 2 and 3, in use, obturator 10 is inserted through an aperture 36 in a suitable rigid grid positioning system 32, preferably registered with a stereotactic gamma imaging system (40 and 42). Images of a mass 38 that contains or may contain an area of interest are then obtained in the context of grid 34 and imager 40/42 and the locations of any regions of interest determined from these images in their X, Y and Z axes calculated. Thus, the location(s) of the regions of interest within and below the grid system are determined. An incision is then made into mass 38 to the previously calculated region)s) of interest, obturator 10 inserted into the incision to the required depth, to provide a real-time indication of the exact location of the region of interest. Obturator 10 is then removed and any required procedure such as the insertion of a biopsy needle and the extraction of tissue performed.

There has thus been described an obturator and method of use thereof that permits real-time localization of an area of interest during stereotactic gamma imaging.

As the invention has been described, it will be apparent to those skilled in the art that the same may be varied in many ways without departing from the spirit and scope of the invention. Any and all such modifications are intended to be included within the scope of the appended claims.

What is claimed is:

1. In combination, a rigid grid positioning system, stereotactic gamma imager, and an obturator for real-time localization of a region of interest during the performance of a surgical procedure comprising:
   a) a rigid grid positioning system and stereotactic gamma imager including a mechanism for the acquisition of images useful in calculating the spatial location of a region of interest in a mass under study;
   b) a generally U-shaped obturator inserted through the rigid grid positioning system comprising:

i) first and second individual and generally parallel capillary tubes defining a continuous path for the introduction thereto and the removal therefrom of a radioactive fluid interconnected at a point of connection between the first and second individual and generally parallel capillary tubes;

ii) a reservoir for the radioactive fluid at the point of connection;

wherein the reservoir is inserted into the mass containing a region of interest and the radioactive fluid provides a marker for the region of interest during subsequent imaging and thereby specific localization of the region of interest during subsequent procedures.

2. The combination of claim 1 wherein the rigid grid positioning system is mechanically co-registered to a stereotactic gamma imager that comprises a set of stereo viewing slant-hole collimators and an array of gamma radiation sensitive crystals and position sensitive photomultipliers.

3. The combination of claim 1 wherein the first and second generally parallel capillary tubes are fabricated from a material that exhibits a higher attenuation of radioactive emissions from the radioactive fluid than the material that comprises the reservoir.

4. A method for real-time imaging and localization of a region of interest in a mass under study comprising exposing the mass using a combination rigid grid positioning system and stereotactic gamma imager, and an obturator for real-time localization of the region of interest comprising:

a) a rigid grid positioning system and stereotactic gamma imager including a mechanism for the acquisition of images useful in calculating the spatial location of a region of interest in a mass under study;

b) a generally U-shaped obturator inserted through the rigid grid positioning system comprising:

i) first and second individual and generally parallel capillary tubes defining a continuous path for the introduction thereto and the removal therefrom of a radioactive fluid interconnected at a point of connection between the first and second individual and generally parallel capillary tubes;

ii) a reservoir for the radioactive fluid at the point of connection;

wherein the reservoir is inserted into the mass containing a region of interest and the radioactive fluid provides a marker for the region of interest during subsequent imaging and thereby specific localization of the region of interest during subsequent procedures.

5. The method of claim 4 wherein the first and second generally parallel capillary tubes are fabricated from a material that exhibits a higher attenuation of radioactive emissions from the radioactive fluid than the material that comprises the reservoir.

6. The method of claim 4 wherein the rigid grid positioning system is mechanically co-registered to a stereotactic gamma imager that comprises a set of stereo viewing slant-hole collimators and an array of gamma radiation sensitive crystals and position sensitive photomultipliers.

* * * * *